United States Patent [19]

Tazuma

[11] Patent Number: 4,621,139

[45] Date of Patent: Nov. 4, 1986

[54] PROCESS FOR THE PREPARATION OF N-TETRATHIODIMORPHOLINE

[75] Inventor: James J. Tazuma, Stow, Ohio

[73] Assignee: The Goodyear Tire & Rubber Company, Akron, Ohio

[21] Appl. No.: 786,391

[22] Filed: Oct. 10, 1985

[51] Int. Cl.$^4$ ............................................. C07D 295/22
[52] U.S. Cl. ......................................................... 544/85
[58] Field of Search .......................................... 544/85

[56] References Cited

U.S. PATENT DOCUMENTS 2,351,657  6/1944  Bayes ..................................... 544/85
2,911,405  11/1959  Gregg, Jr. .............................. 544/85

*Primary Examiner*—Robert W. Ramsuer
*Attorney, Agent, or Firm*—D. O. Nickey

[57] ABSTRACT

There is disclosed a process for the preparation of N-tetrathiodimorpholine wherein an admixture of morpholine and elemental sulfur is oxidized with air or oxygen in the presence of iron salts and iron complexes to yield N-tetrathiodimorpholine.

10 Claims, No Drawings

PROCESS FOR THE PREPARATION OF N-TETRATHIODIMORPHOLINE

TECHNICAL FIELD

The invention relates to a new process for the preparation of N-tetrathiodimorpholine. The invention provides an efficient method of preparing N-tetrathiodimorpholine that avoids costly and corrosive chemicals and yields a stable crystalline product with good shelf life.

BACKGROUND OF THE INVENTION

N-tetrathiodimorpholines have found utility in the rubber industry as sulfur donors and vulcanization accelerators. Previous methods to prepare N-tetrathiodimorpholines have included adding sulfur to a solution of morpholine disulfide. The problem with this preparation is that the preparation of morpholine disulfide is expensive and cumbersome. Morpholine disulfide is prepared by the reaction of morpholine and sulfur monochloride in the presence of alkali in an organic solvent. M. C. Throdahl and M. W. Harman, Ind. Eng. Chem., 43, 421 (1951).

Another prior art methodology for the preparation of N-tetrathiodimorpholines involves the use of halopolysulfides and morpholine. This procedure uses the highly toxic and corrosive halopolysulfides, for example, chlorodisulfide and dichlorpolysulfides.

U.S. Pat. No. 2,911,405 discloses a process for the preparation of N-tetrathiodimorpholines via insertion of sulfur into 4,4-dithiomorpholine and Chemical Abstracts 40, 732-9 describes a process wherein morpholine and sulfur are reacted in the presence of lead oxide. None of the prior art discloses or suggests a process for the preparation of N-tetrathiodimorpholine based on the oxidation of a morpholine/sulfur mixture in the presence of iron salts or iron complexes.

There is a need in the rubber chemical industry for a new process that efficiently and economically produces N-tetrathiodimorpholines which does not require the use of expensive or dangerous starting materials.

DISCLOSURE OF THE INVENTION

There is disclosed a process for the preparation of N-tetrathiodimorpholine which comprises contacting a mixture of morpholine and sulfur at a mole ratio of morpholine to sulfur of from 1:1 to 5:1 with air or oxygen at superatmosphere pressure at a temperature of from 0° C. to 80° C. in the presence of iron salts or iron complexes.

There is further disclosed a process for the preparation of N-tetrathiodimorpholine, the improvement comprising the oxidation of a morpholine sulfur mixture with air or oxygen in the presence of ferric chloride.

There is also disclosed a process for the preparation of N-tetrathiodimorpholine which comprises the steps of:

(a) admixing morpholine and sulfur to a mole ratio of morpholine to sulfur of from 1:1 to 5:1;
(b) contacting the admixture with air or oxygen at elevated pressure and at a temperature from 20° C. to 60° C. in the presence of iron salts or iron complexes:
(d) isolating N-tetrathiodimorpholine.

Through the process of the instant invention, N-tetrathiodimorpholine is obtained by the reaction of morpholine with sulfur in the presence of air or oxygen. A by-product, morpholinium thiosulfate, is also formed. Morpholinium thiosulfate is the major product when the oxidation is conducted without the addition of iron salts or iron complexes. E. M. Peters and W. T. Smith, Jr., Proc. Iowa Acad. Sci. 57, 211 (1950).

An advantage of the instant invention is the use of air or oxygen as the oxidizing agent, thus avoiding costly, corrosive, or toxic chemicals. Through the instant process N-tetrathiodimorpholine can be obtained in 90% selectivity based on reacted morpholine.

Morpholine, the starting material for the instant invention, has the empirical formula $C_4H_9NO$. It has been determined that morpholine from different sources may contain various levels of iron contaminants. The sulfur used in the instant process is conventional rombic sulfur that is in the form of a fine powder. Sulfur normally exists in the $S_8$ rombic form, and when used herein, the term "moles of sulfur" actually refers to gram atoms of sulfur. The mole ratio of morpholine to sulfur can range from 1.0:1.0 to 5.0:1.0. More preferred is the range of 1.0:1.0 to 1.5:1.0.

Representative of the iron salts and iron complexes that are useful in this invention are ferric chloride, ferrous chloride, ferric acetate, ferrous acetate, ferrous ammonium sulfate, ferric bromide, ferrous bromide, ferrous carbonate, ferrocyanides, ferricyanides, ferric fluoride, ferrous fluoride, ferric hydroxides, ferrosoferric hydroxide, ferrous hydroxide, ferrous iodide, ferric nitrate, ferrous nitrate, ferric oxalate, ferrous oxalate, ferric oxide, ferrous oxide, ferric sulfate, ferrous sulfate, ferric sulfide, ferrous sulfide, EDTA iron complexes, and others that are apparent to those skilled in chemistry. The quantity of iron per kilogram of morpholine can range between 0.1 mg and 30 mg. The preferred range is 5 mg to 20 mg.

The admixture of morpholine and sulfur at 20° C. to 60° C. is contacted with oxygen or air at atmospheric or superatmospheric pressure such as ten atmosphere. It should be appreciated that air or air enriched with oxygen at superatmospheric pressure can be employed. Conventional stainless stirred reactors can be used and the reaction is terminated with the disappearance of sulfur.

After the reaction, the slurry is cooled to 15° C. and seeded with crystalline tetrathiodimorpholine. Additionally, this step may be aided by addition of methyl alcohol. After a crystallization period, the mixture may be treated with dilute caustic solution which dissolves the salts and color bodies leaving a nearly white crystalline product. This product analyzes about 95% tetrathiodimorpholine by HPLC. The residual morpholine present in the filtrate effluent can be recovered by fractional distillation.

Best Mode for Carrying Out the Invention

The following examples are offered to further illustrate the novelty and utility of the present invention, but not with the intention of unduly limiting the same.

EXAMPLE 1

To a 500 ml, three-necked flask fitted with a high speed stirrer, gas inlet unit, thermometer and water bath was charged 87 grams of morpholine containing 1 mg of iron as ferric chloride. The resultant mixture was stirred rapidly and oxygen was introduced to the flask. A water bath was used to hold the reaction mixture at 40° C. After one hour most of the sulfur was reacted and the mixture took on a semi-translucent light orange color. The mixture was diluted with 75 ml of methanol and cooled to 15° C. and crystallization was allowed to proceed over a 30 minute period. The product was recovered by diluting the crystallized mixture with 150 ml of 0.7 molar sodium hydroxide solution and by filtration. The product after further washing with water and drying weighed 60.6 grams. This product had excellent shelf life at 50° C. The selectivity of the reaction with respect to morpholine was 90%.

EXAMPLE 2

The procedure in example 1 was used except that morpholine was charged with 1.1 mg of ferrous chloride or 0.5 mg of iron. The reaction required 1.5 hour at 40° C. and yielded 60.3 grams of tetrathiodimorpholine.

EXAMPLE 3

The procedure of Example 2 was used except an equivalent amount of an EDTA (ethylenediaminetetraacetic acid) complex of an iron salt was used. The results were identical to Example 2.

Compounding Study

A compounding study was conducted to compare the product of the instant invention to known sulfur donor accelerators. It was found to be a good replacement for conventional sulfur donor accelerators in various rubber stocks. The physical properties and state of cure in most instances were nearly identical to those of the commercially available control. Overall, the tetrathiodimorpholine prepared according to the instant invention can be considered competitive with material presently used in industry.

Industrial Applicability

The process of the instant invention fulfills a long-felt need in the rubber chemical industry. The importance of amine sulfides as vulcanization accelerators is well established. See M. C. Throdahl and M. W. Harman, Ind. Eng. Chem. 43, 431 (1951). Through the instant process, N-tetrathiodimorpholines can be produced efficiently and economically without the use of corrosive or toxic chemicals.

While certain representative embodiments and details have been shown for the purpose of illustrating the invention, it will be apparent to those skilled in this art that various changes and modifications may be made therein.

Having described the invention in such detail so as to allow one skilled in the art to duplicate the same, the inventor herein claims his invention as follows.

I claim:

1. A process for the preparation of N-tetrathiodimorpholine which comprises contacting a mixture of morpholine and sulfur at a mole ratio of morpholine to sulfur of from 1:1 to 5:1 with air or oxygen at atmospheric or superatmosphere pressure at a temperature of from 0° C. to 80° C. in the presence of iron salts or iorn complexes.

2. The process of claim 1 wherein the iron salt is ferric chloride.

3. The process of claim 1 wherein the iron salt is ferrous chloride.

4. The process of claim 1 wherein 0.1 to 30 mg of iron per kg of morpholine is used.

5. The process of claim 1 wherein the amount of iron is from 5 to 20 mg per kg of morpholine.

6. The process of claim 1 wherein the reaction is carried out at 20° C. to 60° C.

7. The process of claim 1 wherein oxygen is used at atmospheric or superatmospheric pressure.

8. The process of claim 1 wherein air is used at superatmospheric pressure.

9. The process of claim 1 wherein air enriched with oxygen is used at atmospheric or superatmospheric pressure.

10. The process of claim 1 wherein the iron complex is an EDTA complex of an iron salt.

* * * * *